United States Patent [19]

Li et al.

[11] 3,979,473

[45] Sept. 7, 1976

[54] PROCESS FOR THE COLOR STABILIZATION OF INDENE

[75] Inventors: George S. Li, Aurora; Gerald P. Coffey, Cleveland Heights, both of Ohio

[73] Assignee: Standard Oil Company, Cleveland, Ohio

[22] Filed: Dec. 23, 1974

[21] Appl. No.: 535,490

[52] U.S. Cl. ............................ 260/674 R; 203/9; 208/293; 208/297; 260/666.5; 260/669 A
[51] Int. Cl.$^2$ ............................................ C07C 7/18
[58] Field of Search ........ 260/674 R, 666.5, 669 A, 260/674 R, 666.5; 203/9; 208/293, 297

[56] References Cited
UNITED STATES PATENTS

| | | | |
|---|---|---|---|
| 1,206,962 | 12/1916 | Weiss | 208/293 |
| 2,228,788 | 1/1941 | Soday | 260/669 |
| 2,228,789 | 1/1941 | Soday | 260/666.5 |
| 2,228,791 | 1/1941 | Soday | 260/666.5 |
| 2,230,274 | 2/1941 | Soday | 260/674 |
| 2,249,793 | 7/1941 | Soday | 260/674 |
| 2,251,938 | 8/1941 | Jordan | 260/674 |
| 2,257,078 | 9/1941 | Soday | 260/666.5 |
| 2,392,910 | 1/1946 | Franz | 260/669 |
| 2,413,260 | 12/1946 | Soday | 260/674 |

*Primary Examiner*—Delbert E. Gantz
*Assistant Examiner*—C. E. Spresser
*Attorney, Agent, or Firm*—John F. Jones; Sherman J. Kemmer; Evelyn R. Kosman

[57] ABSTRACT

A process for the stabilization of indene against discoloration comprising adding to the indene a minor amount of an insoluble compound selected from the group consisting of neutral, acidic and basic inorganic salts, inorganic acids and organic acids.

4 Claims, No Drawings

PROCESS FOR THE COLOR STABILIZATION OF INDENE

The present invention relates to a method for the color stabilization of indene. More particularly, this invention relates to a process for the stabilization of indene against discoloration by the addition thereto of a minor amount of a compound or compounds selected from the group consisting of neutral, acidic and basic inorganic salts, inorganic acids and organic acids.

Indene is a highly desirable compound for the production of numerous products such as synthetic resins. It is known, however, that commercially available indene derived from such sources as petroleum or coal tar has a tendency to discolor on storage in the presence of light or air, and is therefore not of a polymerizable grade. Due to the tendency of indene to oxidize and/or polymerize, the purification of indene by prior art processes, as fractional distillation, without substantial oxidation or polymerization presents a difficult problem. Additionally, not all of the impurities believed to be responsible for discoloration are removed by distillation since fractionally distilled indene develops further color on standing.

We have found that indene can be readily stabilized against color degradation by the process of the present invention without experiencing any of the above difficulties. In the preferred aspect of the present invention, it is desirable to use neutral, acidic or basic inorganic salts, inorganic acids, and organic acids which are solids and which are substantially insoluble in indene. Although indene-soluble stabilizers are just as effective as the insoluble, crystalline types, the use of insoluble stabilizers has the important advantage of ease of separation from the indene by the standard physical methods of separation, as by decantation, filtration, or centrifugation, thereby eliminatng the possibility of interference of the stabilizer with the free radical polymerization and copolymerization reactions of indene.

The nature of the chemical reaction involved in the stabilization is not clearly understood, but it is believed that the color change may be due to minor impurities in the indene, since many impurities have been identified in the commercial product. It is postulated that the stabilizing compounds of this invention react to form a substance which is more stable than the impurity in its original form.

The preferred stabilizers of this invention are the substantially insoluble, neutral, slightly acidic and slightly basic inorganic salts wherein the cation may be a member of Groups IA, IB, IIA, IIB, IIIA, IVA, VA and VIII of the Periodic Classification of Elements, and the anion may be a member of Group VIIA of the Periodic Classification, or it may be another common anion as for example, a sulfate, thiosulfate, nitrate, phosphate, carbonate, bicarbonate, borate or oxide. Also among the preferred stabilizers are the inorganic acids, such as boric acid and silicic acid.

More preferably the stabilizers of this invention include the insoluble, inorganic acid salts wherein the cation may be aluminum, zinc, cadmium, mercury, copper, silver, iron, cobalt, nickel, silicon, tin, lead, arsenic or antimony, and the anion may be selected from the group consisting of a chloride, sulfate, phosphate or an oxide.

Suitable insoluble organic acids include oxalic acid, malic acid, maleic acid, fumaric acid, itaconic acid citric acid, aconitic acid, 1,2,3-benzenetricarboxylic acid, 1,2,4-benzenetricarboxylic acid, 1,3,5-benzenetricarboxylic acid, 1,2,4,5-benzenetetracarboxylic acid, and acids represented by the formula:

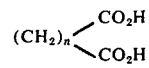

wherein "$n$" is an integer of from 1 to 7, and the like.

The stabilizers of this invention are effective in very low concentrations, ranging from about 0.001 to 2.5 percent by weight in indene, and more preferred are concentrations in the range of from about 0.05 to 1.5 percent by weight.

To evaluate the stabilizing action of the compounds of this invention, the following experiments were performed:

100 Mgs. of the selected compound was added to a test tube containing 3 to 4 mls. of freshly distilled indene, and the test tube was stoppered with a cork stopper. The test tubes were not protected in any way from light or air. After a period of 9 days[1], the degree of color formation in the samples was measured by comparison with Gardner color standards ranging from 1 (the lightest color) to 18, according to the ASTM Test Method D1544-68. The results of these experiments are shown in Table 1.

[1]Stored at room temperature and under normal lighting conditions.

Table I

| Example | Stabilizer | Gardner Color Rating |
|---|---|---|
| 1 | Control (untreated distilled indene) | 3 |
| 2 | KOH | 5 |
| 3 | 2,5-di-tert-amyl hydroquinone | 3 |
| 4 | Copper wire | 2 |
| 5 | $CaSO_4$ | 1 |
| 6 | $NaHCO_3$ | 1 |
| 7 | $Na_2S_2O_3.5H_2O$ | <1 |
| 8 | $Al_2(SO_4)_3.18H_2O$ | <1 |
| 9 | Citric acid | <1 |
| 10 | Boric acid | <1 |
| 11 | $ZnCl_2$ | <1 |
| 12 | 1N HCl | <1 (Sl. cloudy) |

The data in the above table show the effectiveness of the inorganic neutral, acidic, and slightly basic salts and the inorganic and organic acids as color stabilizers for indene, whereas strongly basic compounds such as KOH (Example 2) promote color formation in indene.

We claim:

1. A process for the stabilization of indene against color formation consisting of adding to the indene an insoluble solid stabilizer selected from the group consisting of aluminum sulfate and zinc chloride in a concentration from about 0.001 to 2.5 percent by weight based on indene, and subsequently separating the stabilizer from the stabilized product.

2. The process in claim 1 wherein the insoluble stabilizer is separated from the stabilized indene by filtration.

3. The process in claim 1 wherein the insoluble stabilizer is separated from the stabilized indene by decantation.

4. The process in claim 1 wherein the insoluble stabilizer is separated from the stabilized indene by centrifugation.

* * * * *